United States Patent [19]

Markin et al.

[11] Patent Number: 5,351,801
[45] Date of Patent: Oct. 4, 1994

[54] AUTOMATED LABORATORY CONVEYOR SYSTEM

[75] Inventors: Rodney S. Markin, Omaha, Nebr.; Eldon L. Tackett, Neola, Iowa; Stephen J. Hoskinson, Omaha, Nebr.

[73] Assignee: Board of Regents - Univ. of Nebraska, Lincoln, Nebr.

[21] Appl. No.: 75,682

[22] Filed: Jun. 7, 1993

[51] Int. Cl.⁵ .......................................... B65G 37/00
[52] U.S. Cl. ............................... 198/346.1; 198/349; 198/349.6; 198/465.1
[58] Field of Search ................... 198/349, 349.6, 465.1, 198/465.2, 346.1, 346.2

[56] References Cited

U.S. PATENT DOCUMENTS

| | | | |
|---|---|---|---|
| 3,527,087 | 9/1970 | Converse et al. | 198/346.1 |
| 3,803,556 | 4/1974 | Duffy | 198/349 |
| 4,483,433 | 11/1984 | Fischer et al. | 198/346.2 |
| 4,506,777 | 3/1985 | Kampf | 198/465.2 |
| 4,805,759 | 2/1989 | Rochet et al. | 198/346.1 |
| 4,958,716 | 9/1990 | Matsuo et al. | 198/465.1 |
| 4,971,189 | 11/1990 | Fleming et al. | 198/349 |

*Primary Examiner*—Joseph E. Valenza
*Attorney, Agent, or Firm*—Zarley, McKee, Thomte, Voorhees & Sease

[57] ABSTRACT

An automated laboratory conveyor system includes a conveyor track arranged in a closed loop to continuously transport a specimen carrier having a laboratory specimen therein. A receiving station marks an individual specimen carrier to identify the carrier with a particular specimen. The receiving station includes an apparatus for placing an identified specimen carrier on the conveyor track. An archiving station is provided along the track to remove a predetermined specimen carrier therefrom for archival purposes. The receiving station and archiving station are both connected to a central control unit which is connected to the conveyor track and the laboratory information system to control the entire automated laboratory conveyor system. At least one work station is located along the conveyor track for performing a predetermined test on a particular specimen. Each work station includes a gate apparatus for transferring the selected specimen carrier to a work station. After the predetermined test has been conducted, the specimen carrier is placed back on the conveyor track loop by a second gate on the conveyor track. The first gate includes a reader for identifying a particular specimen carrier being conveyed by the conveyor track. The reader is also connected to the central control unit, as are the gates for each work station, so that particular specimens may be directed to an appropriate work station by the central control unit.

12 Claims, 10 Drawing Sheets

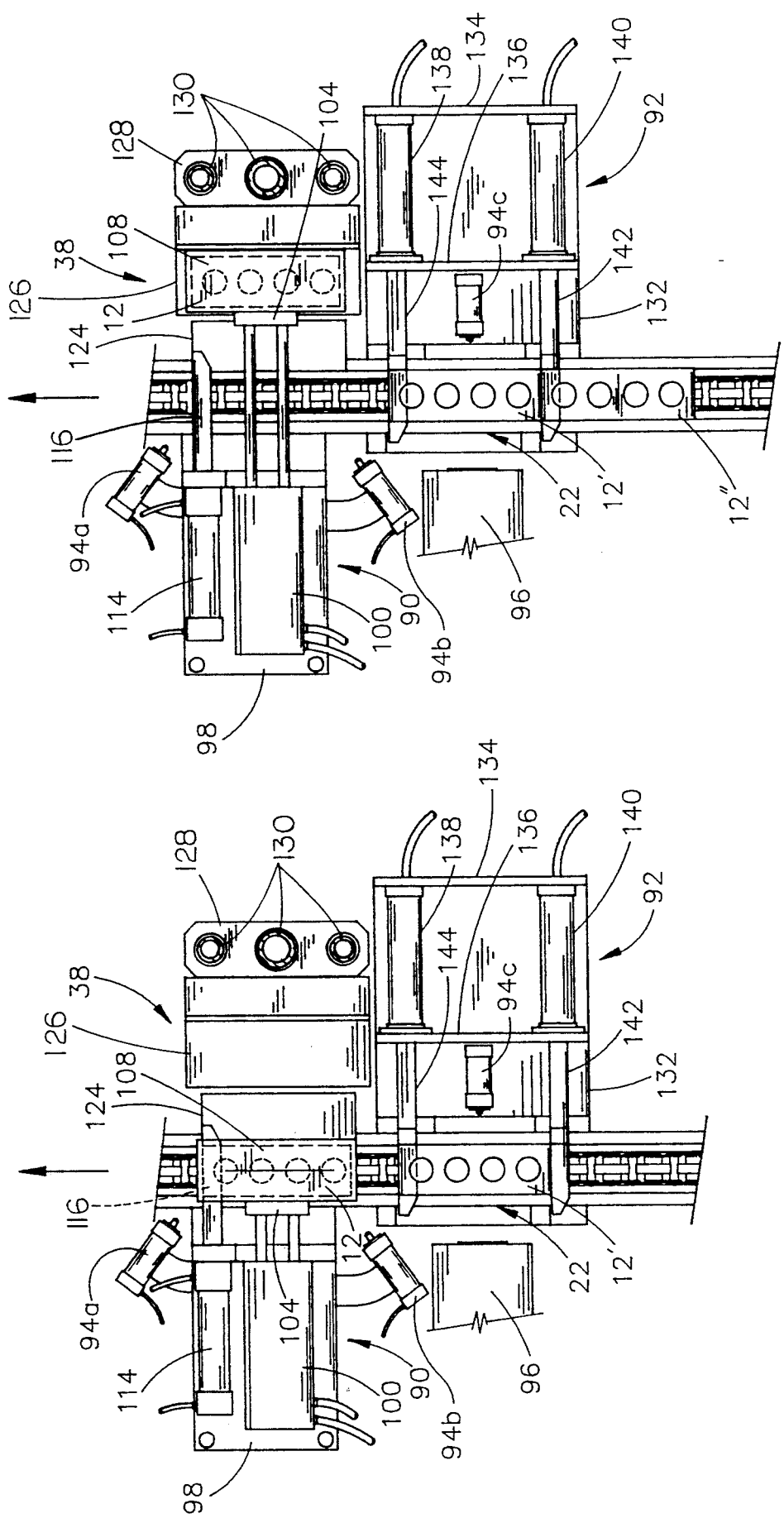

AUTOMATED LABORATORY CONVEYOR SYSTEM

TECHNICAL FIELD

The present invention relates generally to systems for the automation of clinical laboratories, and more particularly to a conveyor system utilized in transporting specimens throughout an automated laboratory.

BACKGROUND OF THE INVENTION

Clinical laboratory testing has been changed and improved remarkably over the past 70 years. Initially, tests or assays were performed manually, and generally utilized large quantities of serum, blood or other materials/body fluids. As mechanical technology developed in the industrial work place, similar technology was introduced into the clinical laboratory. With the introduction of new technology, methodologies were also improved in an effort to improve the quality of the results produced by the individual instruments, and to minimize the amount of specimen required to perform each test.

More recently, instruments have been developed to increase the efficiency of testing procedures by reducing turnaround time and decreasing the volumes necessary to perform various assays. Present directions in laboratory testing focus on cost containment procedures and instrumentation. Laboratory automation is one area in which cost containment procedures are currently being explored. Robotic engineering has evolved to such a degree that various types of robots have been applied in the clinical laboratory setting.

The main focus of prior art laboratory automation relies on the implementation of conveyor systems to connect areas of a clinical laboratory. Known conveyor systems in the laboratory setting utilize separate conveyor segments to move specimens from a processing station to a specific laboratory work station. In order to obtain cost savings, the specimens are sorted manually, and test tubes carrying the specimens are grouped in a carrier rack to be conveyed to a single specific location. In this way, a carrier will move a group of 5-20 specimens from a processing location to a specific work station for the performance of a single test on each of the specimens within the carrier rack.

With the advent of the inventors' new laboratory automation system, as described in co-pending patent application Ser. No. 07/997,281, entitled "METHOD FOR AUTOMATIC TESTING OF LABORATORY SPECIMENS", the inventor has provided a laboratory automation system which requires a different type of conveyor system for the transport of specimens throughout the laboratory. The new laboratory automation system of the co-pending patent application calls for the identification and conveyance of an individual patient's specimen to at least one of a plurality of separate work stations. As discussed above, prior art conveyor systems were based on increasing the quantity of specimens conveyed to a single work station to obtain cost savings. For this reason, prior art conveyor systems were typically "point to point" wherein a plurality of specimens were moved from a processing location to a single work station for completion of a test on all such specimens, at which time the plurality of specimens were returned to the processing station. Such conveyor systems suffer several drawbacks.

First, it is not possible to expedite the processing of a single specimen which is included within a plurality of specimens conveyed to a specific work station. Rather, all of the specimens are conveyed to the work station, all of the specimens are tested, and then all of the specimens are returned to the processing station. Individualized, or prioritization, is not possible with such a conveyor system.

In addition, conducting more than one test on an individual specimen is time consuming. Again, an individual specimen is included in a group of specimens which is transported to a single work station. Before a second test may be performed on any individual specimen, the first test at the work station must be completed on all specimens included in the carrier rack transported to the particular work station. After completion of the first testing procedure at the first work station, all of the specimens are returned to the processing station, at which time individual specimens may then be redirected to a different carrier rack for transport with a plurality of other specimens to a second work station, wherein a multitude of identical tests are performed on a plurality of specimens in that second carrier rack.

SUMMARY OF THE INVENTION

It is therefore a general object of the present invention to provide an improved conveyor system for transporting specimens throughout an automated laboratory system.

Another object of the present invention is to provide an automated conveyor system which is capable of directing individual specimens to a plurality of separate work station.

Still another object is to provide a conveyor system which is located above the usable laboratory floor space, to permit more efficient use of the defined laboratory space.

A further object of the present invention is to provide a conveyor system with elevators for vertically transporting specimens from a conveyor to a work station, and back to the conveyor.

Yet another object of the present invention is to provide a conveyor system with gates for directing individual specimens to predetermined work stations.

These and other objects will be apparent to those skilled in the art.

The automated laboratory conveyor system of the present invention includes a conveyor track arranged in a closed loop to continuously transport a specimen carrier having a laboratory specimen therein. A receiving station is provided along the track which is connected to a laboratory information system having identification and instructional data with respect to a particular specimen, and which marks an individual specimen carrier to identify the carrier with a particular specimen as it is conveyed throughout the conveyor system. The receiving station includes an apparatus for placing an identified specimen carrier on the conveyor track, so as to insert the carrier in the system. An archiving station is provided along the track to remove a predetermined specimen carrier therefrom for archival purposes. The receiving station and archiving station are both connected to a central control unit which is connected to the conveyor track and the laboratory information system to control the entire automated laboratory conveyor system. At least one work station is located along the conveyor track for performing a predetermined test on a particular specimen. Each work station includes a gate apparatus for transferring the selected specimen carrier from the conveyor track to a work station track, for transport to a work station. After the predetermined test has been conducted, the specimen carrier is placed on a work station track and is placed back on the conveyor track loop by a second gate on the conveyor track. The first gate, for removing a specimen from the conveyor track, includes a reader for identifying a particular specimen carrier being conveyed by the conveyor track. The reader is also connected to the central control unit, as are the gates for each work station, so that particular specimens may be directed to an appropriate work station by the central control unit.

BRIEF DESCRIPTION OF THE DRAWINGS

FIG. 7 is a view similar to FIG. 6, with a second specimen carrier retained in position spaced from a first specimen carrier located in the conveyor gate;

FIG. 8 is a view similar to FIG. 7, showing transfer of the first specimen carrier to an elevator;

DESCRIPTION OF THE PREFERRED EMBODIMENT

Figure 1:
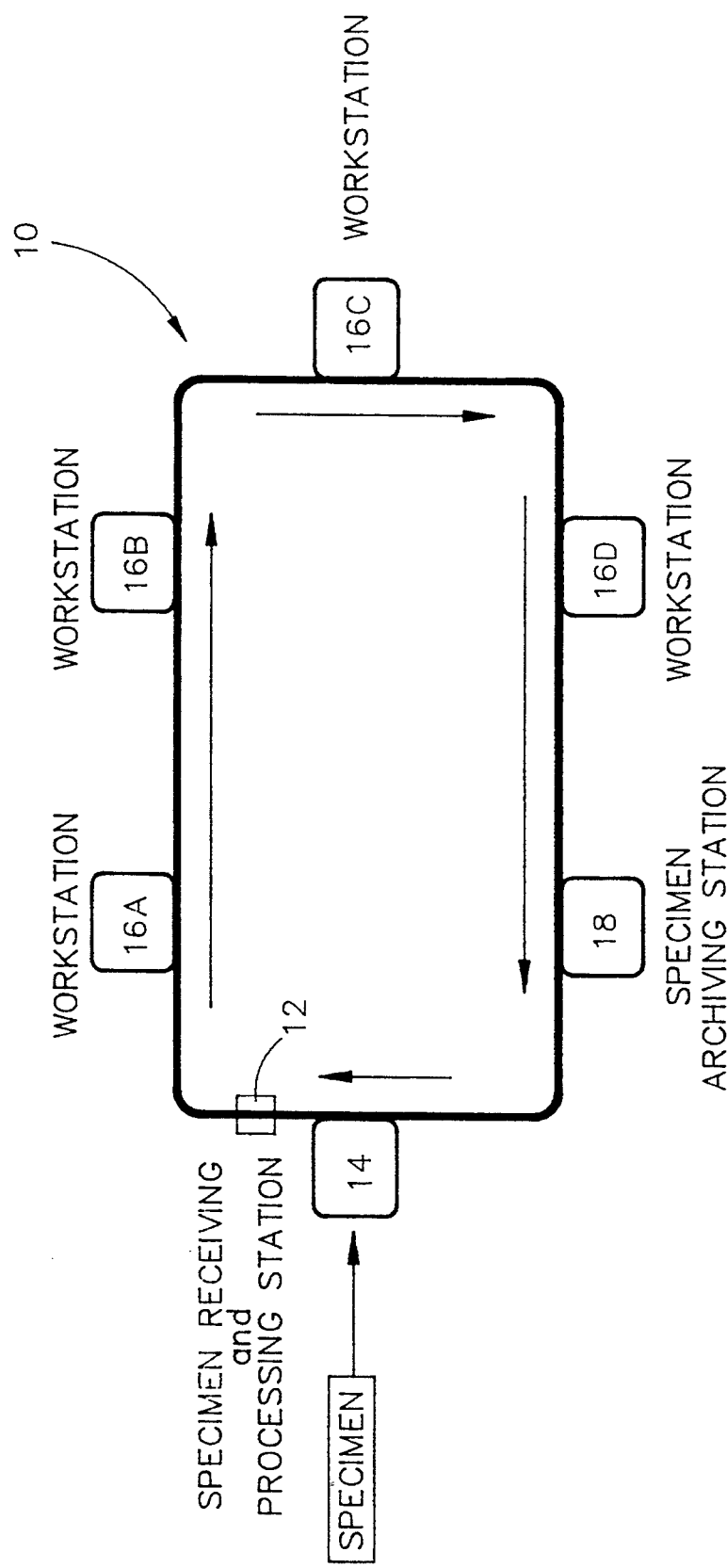
FIG. 1 is a schematic diagram of specimen movement on the conveyor system of the present invention throughout a laboratory automation system.

Referring now to the drawings, wherein similar or corresponding parts are identified with the same reference numeral, and more particularly to FIG. 1, a schematic diagram of a laboratory automation system is shown which includes the conveyor system 10 of the present invention to transport a specimen carrier ( shown schematically at reference numeral 12) from a processing and receiving station 14, among a plurality of work stations 16 and ultimately to a specimen archiving station 18.

As discussed more specifically in the co-pending application described above, the conveyor system of the present invention forms a part of a laboratory automation system (LAS) which works in conjunction with a laboratory information system (LIS) and a hospital information system (HIS). The LIS assigns the task of physically obtaining a specimen, which, once obtained, is then introduced into the LAS. The LAS takes the place of prior art manual testing procedures, and may include the reporting of the test results to the LIS. The LIS communicates with the LAS to order specific tests related to a specific specimen and receive the results of those tests. The LIS also communicates with the HIS to report test results for accounting and insurance purposes. The LIS reports either to the doctor via a separate work station, or via the HIS, to report the results of the requested tests performed by the LAS.

Figure 2:
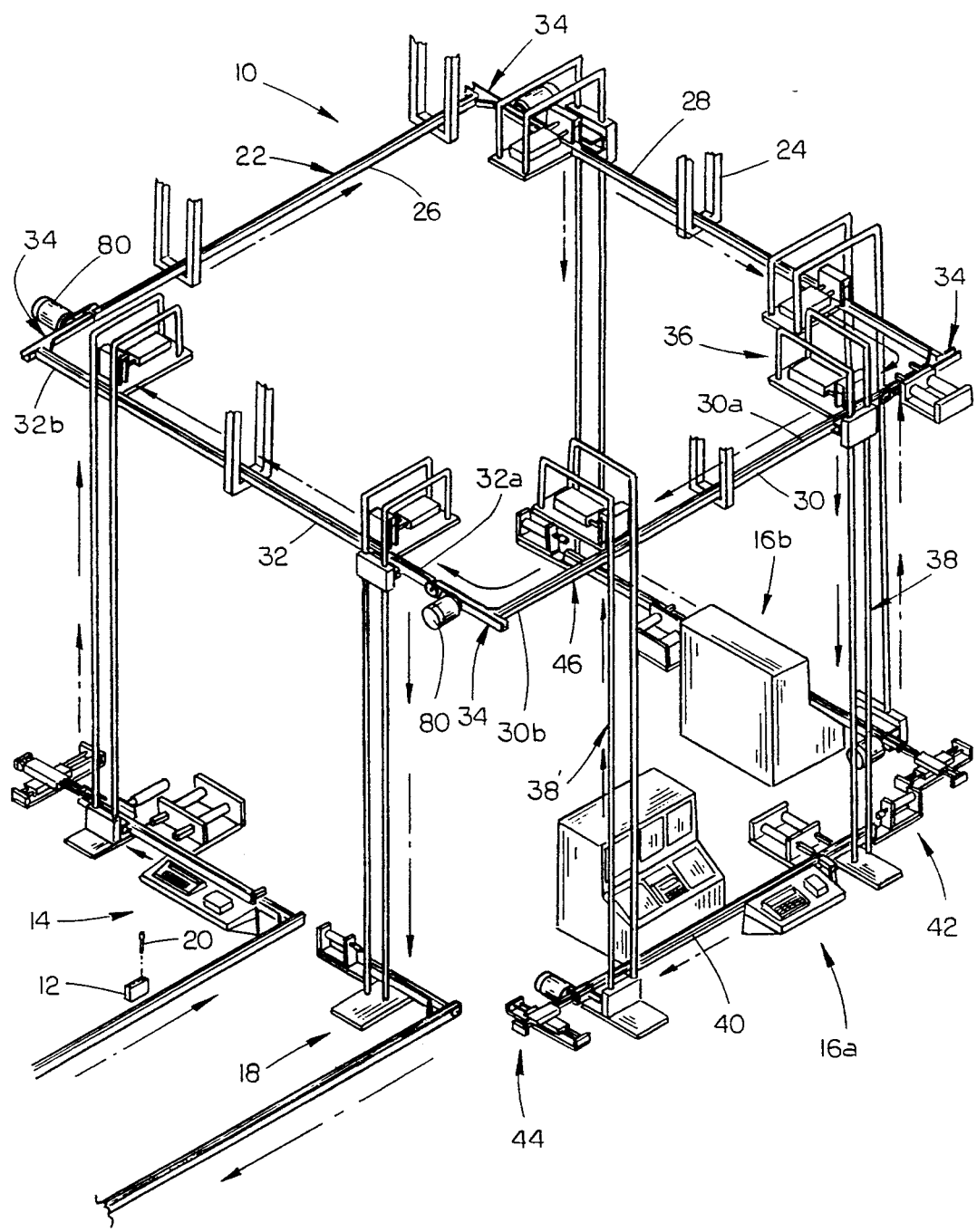
FIG. 2 is a perspective view of the conveyor system of the present invention interconnected by elevators to several work stations.

In general, a specimen arrives at specimen receiving and processing station 14, where the specimen is entered on conveyor system 10. During the assignment of the task of obtaining a specimen, the LIS would also provide a bar code label marked with an appropriate patient identification code for application to an appropriate specimen container, such as a test tube. Since most specimen tubes are not designed for transport on a conveyor system, a separate specimen carrier 12, shown in FIG. 2, is provided to support an individual specimen tube 20 on conveyor system 10. At specimen receiving and processing station 14, the carrier 12 identification code is entered into the computer system to correlate with the specimen tube, so that the specimen tube 20 and carrier 12 may be tracked and directed throughout the conveyor system 10. In a fully automated system this information is entered in the system by scanning the bar code label applied to the tube.

In general, as shown in FIG. 1, conveyor system 10 is preferably a continuously moving conveyor which will move specimen carriers 12 in a generally closed loop system. At the receiving and processing station 14, the carrier assignment is entered into the LAS to determine which work stations the specimen must utilize, the order in which the stations are to be utilized, and any other pertinent information with respect to priority or turnaround time.

While FIG. 1 shows only four specific work stations 16a, 16b, 16c, and 16d, a conventional clinical laboratory could have a much greater number of stations throughout a facility. The closed loop system of conveyor 10 permits a specimen to stop at any given work station in any particular order. Thus, if time constraints require that the test of work station 16b be performed first, and that a test of work station 16a be performed at some time after the test of work station 16b, the specimen can travel on conveyor system 10 past work station 16a, directly to work station 16b, for immediate testing. Carrier 12 may then be rerouted on conveyor system 10 to follow the closed loop around to the next appropriate work station assigned to that particular specimen. Once the testing has been completed, the specimens are forwarded to specimen archiving station 18 for removal from conveyor system 10 for appropriate storage.

Referring now to FIG. 2, conveyor system 10 generally includes a conveyor track 22 preferably supported from the ceiling of a structure by supports 24 so as to hang at a predetermined height preferably above the equipment and persons working within a laboratory. Conveyor track 22 is arranged in a closed loop including track lengths 26, 28, 30 and 32 which are interconnected by corner apparatus 34 to permit continuous running of conveyor track 22 in a single direction.

Conveyor track 22 moves specimen carrier 12 around the various work stations of a laboratory, to enable selective removal of a specimen carrier 12 at any one of a plurality of specific work stations. FIG. 2 has been simplified to incorporate only the general features of the conveyor system 10. Thus, FIG. 2 includes specimen processing and receiving station 14, a pair of work stations 16a and 16b, and the specimen archiving station 18. Other work stations may be introduced at any desired location along the conveyor track loop 22.

Work stations 16a and 16b incorporate the same elements of conveyor system 10, and therefore only the elements of work station 16a will be described in detail herein. In general, an exit gate 36 transfers a specimen carrier 12 from conveyor track 22 to an elevator 38, which lowers the specimen carrier to a work station conveyor track 40. A pusher apparatus 42 transfers the specimen carrier from elevator 38 to work station track 40. After the desired testing has occurred at work station 16a, the specimen carrier is moved along work station track 40 to a receiver apparatus 44 which transfers the specimen carrier to a second elevator 38'. Elevator 38' raises the specimen carrier to conveyor track 22 where an entrance gate 46 then transfers the specimen carrier onto conveyor track 22. Thus, each individual work station includes an exit gate and associated elevator and pusher apparatus to lower a specimen carrier from the conveyor track to the work station track, and a receiver apparatus and associated elevator and entrance gate to move the specimen carrier from the work station track back up to the conveyor track.

Figure 5:
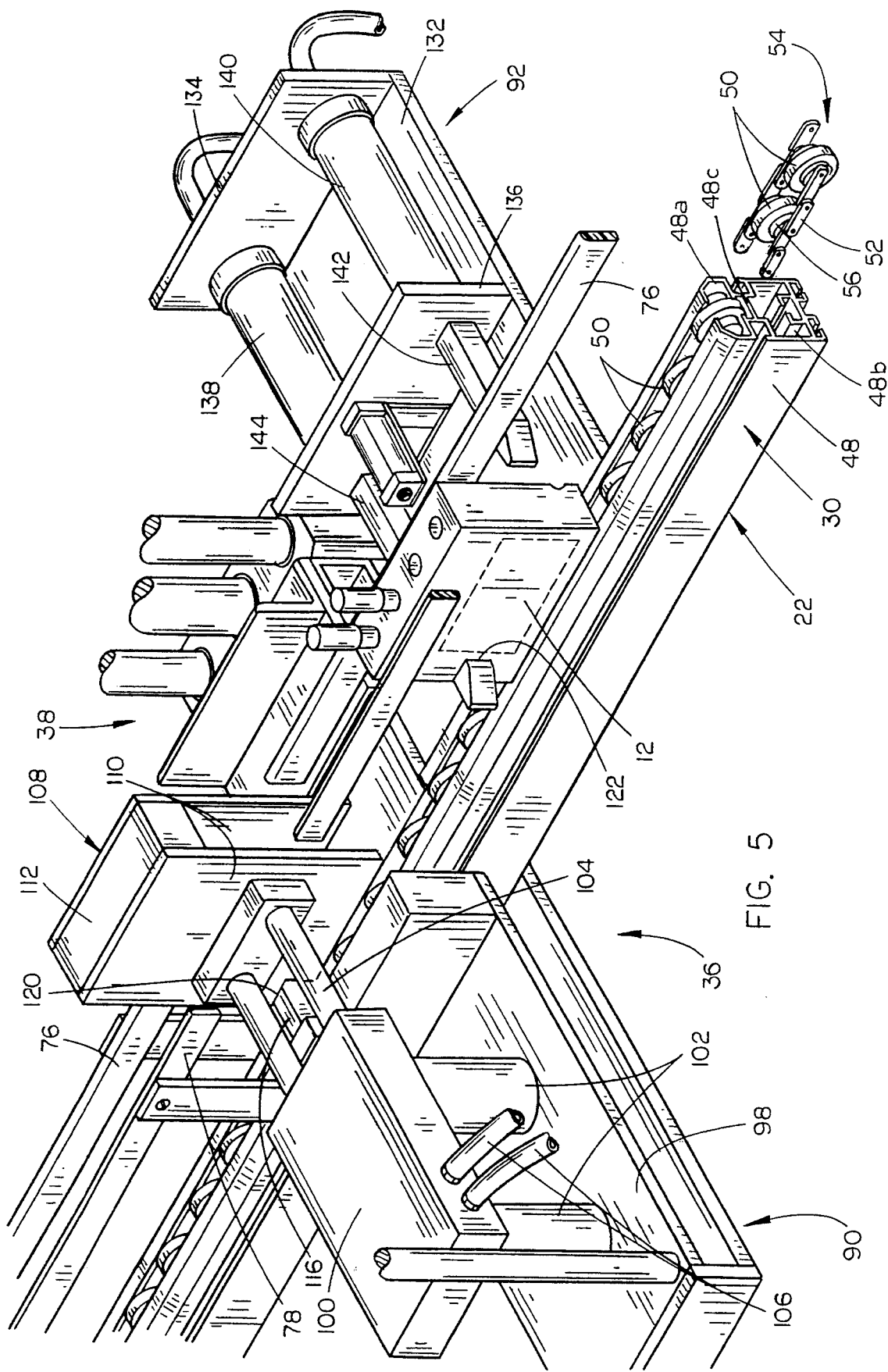
FIG. 5 is a perspective view of a conveyor gate for removing a specimen carrier from the conveyor track.

Referring now to FIG. 5, conveyor track length 30 is preferably formed of generally H-shaped channel 48 having an upper section 48a separated from a lower section 48b by a crossbar 48c. A plurality of rollers 50 are connected by chain lengths 52 to form a continuous roller chain 54 operably mounted in upper and lower portions 48a and 48b of channel 48. A cylindrical bearing 56 mounted in each roller 50 is located to contact cross member 48c of channel 48, and thereby rotate rollers 50. In this fashion, the circumferential surface of each roller 50 will move at a greater velocity than the circumferential surface of cylindrical bearing 56, because of the greater diameter. For the same reason, the relative movement of a specimen carrier 12 riding on rollers 50, will have a greater longitudinal velocity than that of the roller chain 54. In instances where the specimen carrier 12 will travel relatively long distances, it is possible to utilize relatively slow moving roller chains with rollers having a large diameter relative to the cylindrical bearing, to dramatically increase the velocity of specimen carriers moving along the track length 30.

Figure 3:
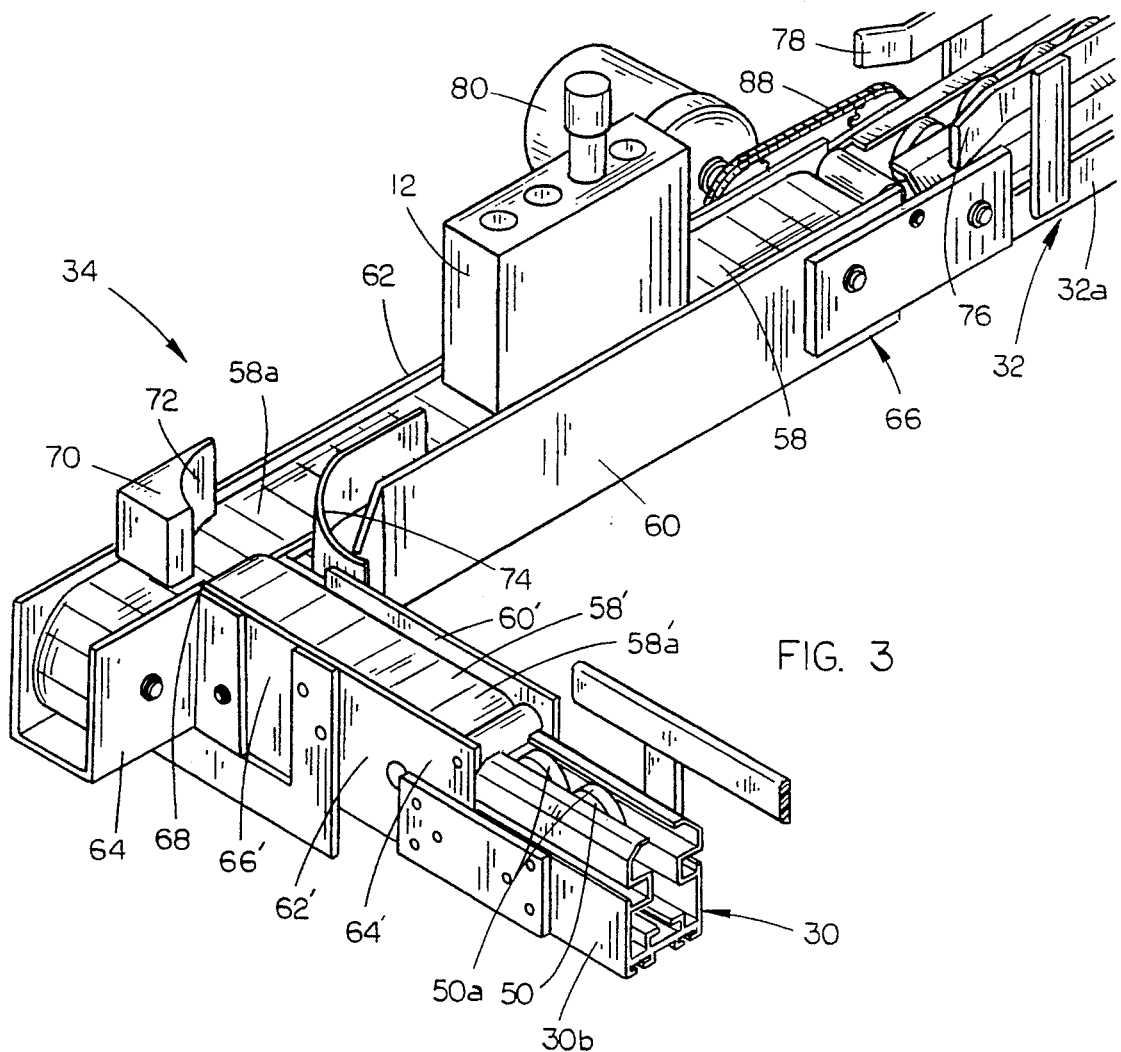
FIG. 3 is a perspective view of a corner apparatus of the conveyor system.

As shown in FIG. 2, conveyor track 22 moves continuously in a single direction, along a closed loop. In order to turn corners, a special corner apparatus 34 is provided connecting the downstream end of one conveyor track length with the upstream end of a subsequent conveyor track length. FIG. 3 shows a typical corner apparatus 34 connecting the downstream end 30b of track length 30 with the upstream end 32a of a subsequent track length 32. Corner apparatus 34 includes a continuous loop conveyor belt 58 mounted between a pair of opposing side walls 60 and 62 and extending from a first upstream end 64 to a downstream end 66. Conveyor belt 58 and side walls 60 and 62 are oriented at an angle with respect to track length 30 and are in alignment with track length 32. The downstream end 30b of track length 30 is aligned with a second continuous loop conveyor belt 58' having side walls 60' and 62' and extending from an upstream end 64' to a downstream end 66'. The downstream end 66' of second conveyor belt 58' is aligned with an opening 68 in side wall 60 of first conveyor belt 58. The upper surface 50a of rollers 50 is located slightly higher than the upper surface 58'a of conveyor belt 58' at the upstream end 64' of conveyor belt 58', such that specimen carrier 12 will project outwardly over belt 58' and drop onto the upper surface 58'a thereof. Similarly, the upper surface 58'a of conveyor belt 58' is located slightly higher than the upper surface 58a of conveyor belt 58 at opening 68. As specimen carrier 12 drops onto moving belt 58, the motion of belt 58 will pull specimen carrier 12 off of belt 58' and in the direction of track length 32.

An outer guide rail 70 is mounted to side wall 62 on corner apparatus 34 and includes an arcuate wall 72 thereon which will redirect the direction of specimen carrier 12 onto conveyor belt 58. Arcuate wall 72 provides a smooth transition from track length 30 and conveyor belt 58' to conveyor belt 58. An inner guide rail 74 is mounted on side wall 60 and also serves to guide specimen carrier 12 on corner apparatus 34. Inner guide rail 74 is formed of an elongated strip of material bent into an arcuate shape generally paralleling the arcuate wall 72 of outer guide rail 70.

Figure 4:
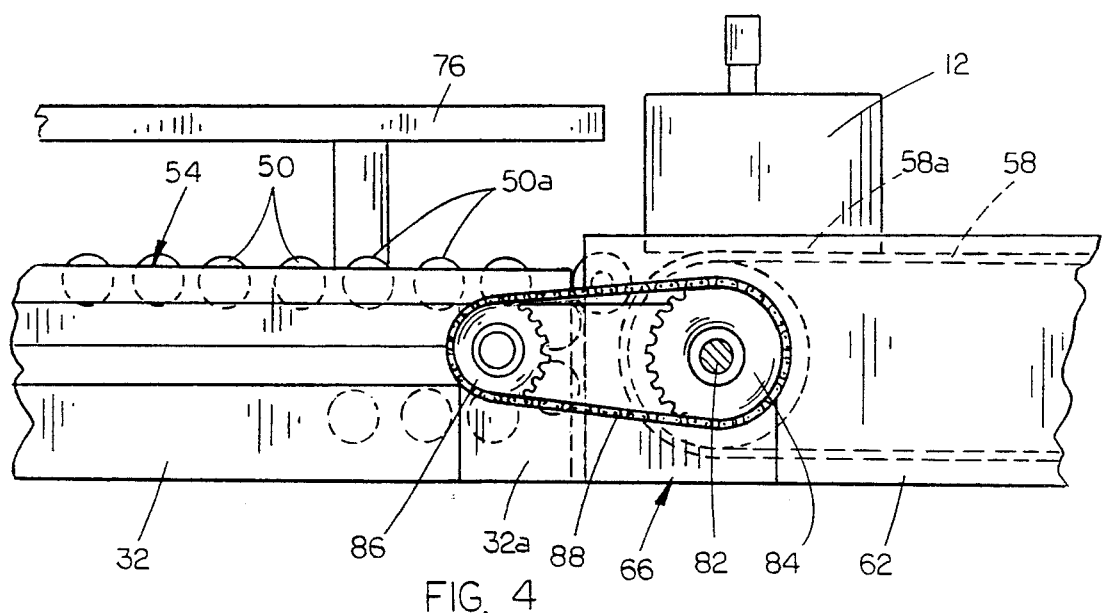
FIG. 4 is a side view of a portion of the conveyor track interconnecting a corner apparatus with a conveyor length.

As shown in FIG. 4, the downstream end 66 of corner apparatus side walls 60 and 62 is connected to the upstream end 32a of track length 32. The upper surface 58a of conveyor belt 58 is raised slightly above the top surface 50a of rollers 50 where corner apparatus 34 connects with track length 32. In this way, specimen carrier 12 will drop slightly downwardly onto the roller chain 54 as it leaves conveyor belt 58. Specimen carrier 12 is retained on rollers 50 by opposing guardrails 76 and 78, as shown in FIG. 3.

Referring again to FIG. 2, each straight length of conveyor track 26, 28, 30 and 32 is preferably independently driven by a motor 80. As shown in FIG. 4, motor 80 drives a drive shaft 82 connected to conveyor belt 58, as well as a drive gear 84. A second gear 86 is connected to drive gear 84 by a drive chain 88 to cause movement of roller chain 54, as shown in FIG. 4. The independent operation of the track lengths 26–32 permits adjustment of the velocity of the specimen carrier along the associated track length. Thus, long track lengths with few or no work station gates may proceed at a very rapid pace, while it may be desirable to move the specimen carrier at a slow velocity where a plurality of exit and entrance gates are utilized on a conveyor track length.

Referring now to FIGS. 5–8, exit gate 36 includes three integrated apparatus to transfer a selected specimen carrier 12 from conveyor track 22 to elevator 38. First, a transfer unit 90 is mounted directly opposite elevator 38, and serves to physically move specimen carrier 12 from conveyor track 22 to elevator 38. Second, a restrainer unit 92 is mounted upstream of transfer unit 90 on conveyor track 22, and is designed to selectively restrain specimen carriers 12 from interfering with the operation of transfer unit 90. Finally, a sensor array 94 including three individual sensors 94a, 94b and 94c are located relative to transfer unit 90 and restrainer unit 92 to detect the presence or absence of specimen carriers 12. An electronic code reader 96 is additionally utilized to identify individual specimen carriers, and is electrically interconnected with the conveyor system control unit so as to locate and identify the individual specimen carriers 12.

Referring to FIG. 5, transfer unit 90 includes a base 98 which supports a pneumatic cylinder 100 spaced above base plate 98 by a pair of support legs 102. Cylinder 100 includes an operable plunger 104 which is extendable and retractable in response to pneumatic pressure applied through pneumatic lines 106.

An inverted channel-shaped housing 108 is mounted on the free end of plunger 104 for movement therewith, and includes a pair of parallel spaced apart vertical side walls 110 and a cross member 112 connecting the upper ends of side walls 110. Cylinder 100 is oriented perpendicular to conveyor track 22 such that housing 108 is oriented with side walls 110 parallel to the longitudinal axis of conveyor track 22. FIG. 5 shows plunger 104 and housing 108 in the retracted position with side walls 110 aligned directly over conveyor track 22 such that specimen carriers 12 may pass completely through housing 108 while traveling along conveyor track 22 on rollers 50. A break in guardrails 76 and 78 permits extension and retraction of housing 108 over conveyor track 22. Preferably, side walls 110 are spaced apart a distance slightly wider than the distance between guardrails 76 and 78. On the downstream side of housing 108, guardrails 76 and 78 are flared slightly so that a carrier 12 will not catch the guardrail ends.

Figure 6:
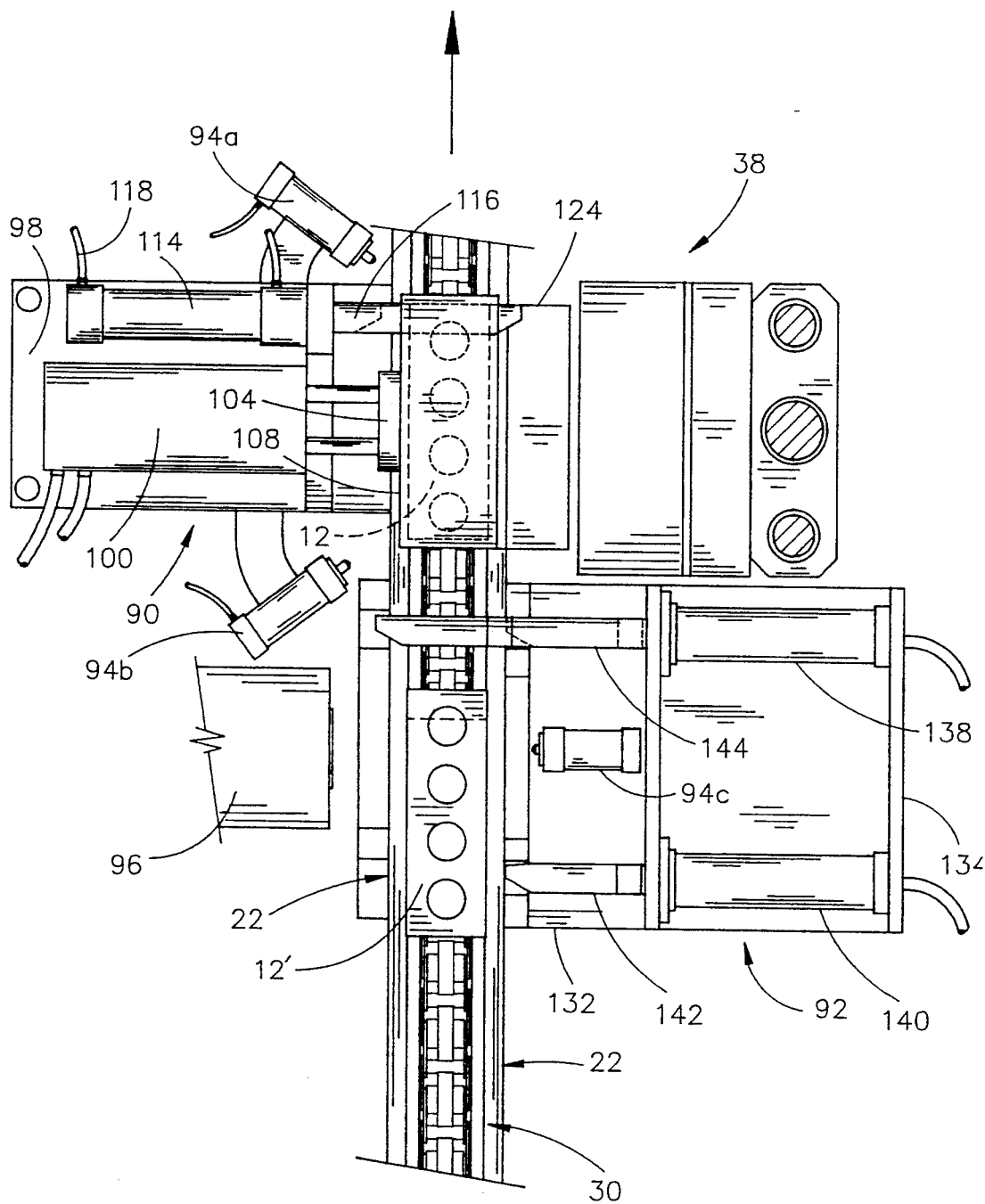
FIG. 6 is a top view of the gate shown in FIG. 5.

Referring now to FIG. 6, an auxiliary pneumatic cylinder 114 is mounted on base 98 parallel to cylinder 100 and downstream thereof, with respect to conveyor track 22. Auxiliary cylinder 114 includes an extendable arm 116 which is shown extended in FIG. 6, with the retracted position shown in broken lines in the drawing. Air lines 118 provide the appropriate force to extend or retract arm 116.

Sensors 94a and 94b are also mounted to base plate 98 and are oriented to detect the presence or absence of a specimen carrier 12 within housing 108. The length of specimen carrier 12 is slightly less than the length of housing 108, such that specimen carrier 12 will be retained completely within housing 108 when arm 116 is extended, as shown in FIG. 6.

FIGS. 7 and 8 show cylinder 100 transferring specimen carrier 12 from conveyor track 22 to elevator 38. Cylinder 100 is operated so as to extend the plunger 104 and thereby shift housing 108 to the position shown in FIG. 8, thereby shifting specimen carrier 12 within housing 108. Arm 116 prevents specimen carrier 12 from moving out of housing 108 as it is shifted off of conveyor track 22. As shown in FIG. 5, a notch 120 in side walls 110 receives arm 116, so as to locate specimen carrier 12 within the confines of housing 108. A corresponding notch 122 in carrier 12, receives arm 116 therethrough.

Figure 9:
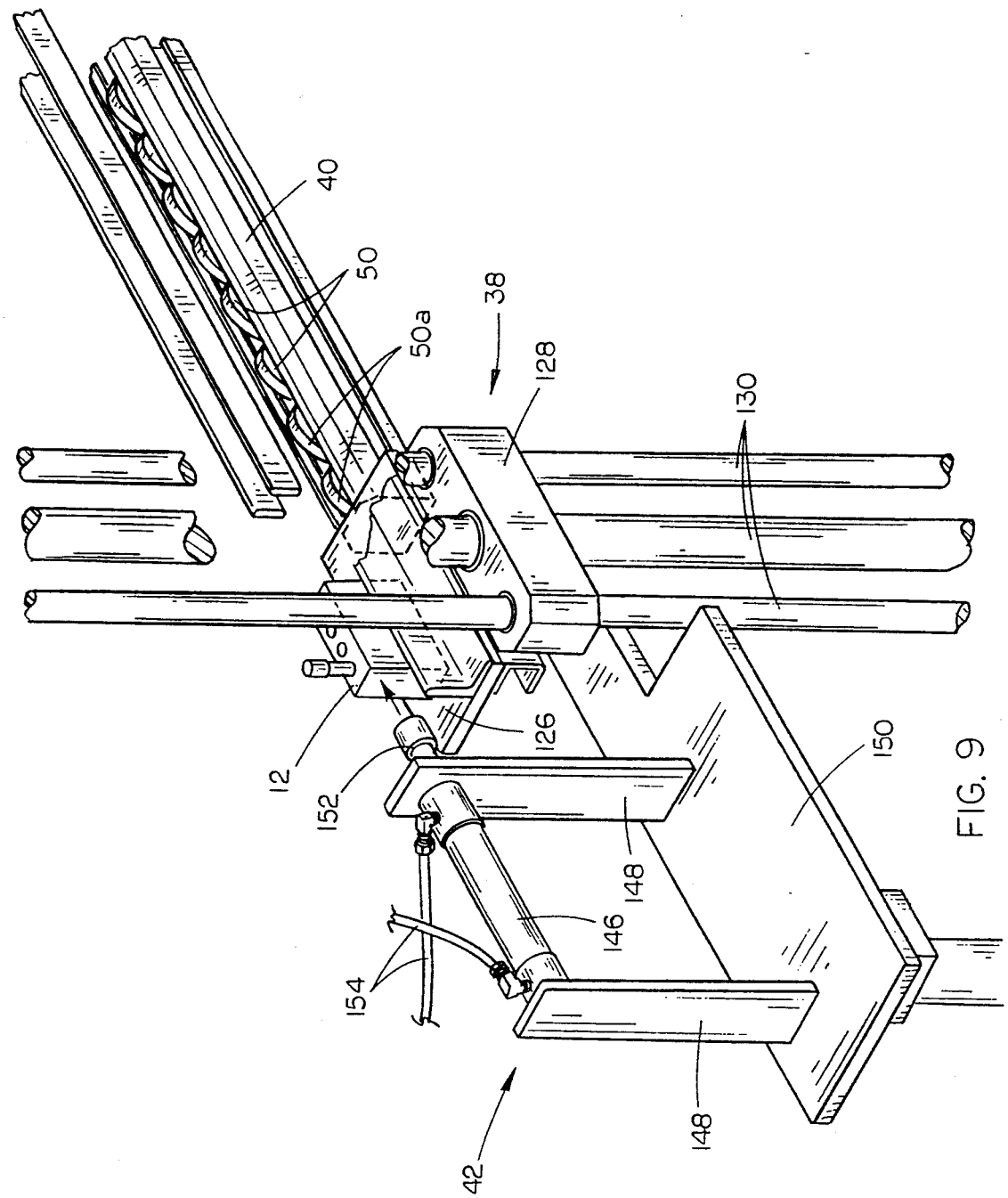
FIG. 9 is a perspective view of the lower end of an elevator showing transfer of a specimen carrier from the elevator to a work station track.

In order to smoothly transfer specimen carrier 12 from track 22 to elevator 38, a short auxiliary platform 124 is mounted on conveyor track 22 and extends outwardly towards elevator 38. The top surface of platform 124 is slightly below the top surface 50a of rollers 50 to permit easy lateral movement of specimen carrier 12 off of rollers 50 and onto platform 124, as housing 108 is shifted outwardly. An elevator platform 126 has an upper surface slightly below the upper surface of auxiliary platform 124, to receive specimen carrier 12 thereon. Elevator platform 126 is mounted to a base 128 which is operably mounted to vertical shafts 130. Base 128 is vertically moveable along shafts 130 so as to lower specimen carrier 12 to a work station conveyor track 40, as shown in FIG. 9. Once platform 126 has been lowered to a position where any specimen tubes 20 in specimen carrier 12 have cleared the lower end of housing 108, housing 108 is retracted on plunger 104 to the position shown in FIG. 5, aligned over conveyor track 22.

Restrainer unit 92 is mounted along conveyor track 22 upstream of transfer unit 90, and restrains subsequent specimen carriers 12' and 12" as shown in FIG. 7 and 8, from interfering with the operation of housing 108. As shown in FIG. 5, restrainer unit 92 includes a base 132 connected to conveyor track 22, with a pair of upright support walls 134 and 136 mounted thereon. Support walls 134 and 136 are parallel and spaced apart, and are parallel and spaced away from conveyor track 22. A pair of first and second pneumatic cylinders 138 and 140 are mounted between support walls 134 and 136, and have extendable arms 142 and 144, respectively, extending through apertures in support wall 136. Cylinders 138 and 140 are oriented perpendicularly to conveyor track 22, with arms 142 and 144 located so as to project over track 22 when operated to the extended position. FIG. 5 shows arm 144 in the extended position, received within notch 122 on specimen carrier 12, retaining specimen carrier 12 in a restrained position on conveyor track 22. Arm 142 is shown in the retracted position, permitting passage of specimen carriers thereby.

As shown in FIG. 7, arm 144 is extended so as to restrain specimen carrier 12' while specimen carrier 12 is transferred to elevator 38. Sensor 94c detects the presence or absence of a specimen carrier to be restrained by arm 144. Arm 142 is shown extended in both FIGS. 7 and 8, and will restrain a second specimen carrier 12" on conveyor track 22 while specimen carrier 12' is released for transfer by transfer unit 90, or released to pass freely along conveyor track 22 past transfer unit 90.

A code reader 96 is located adjacent conveyor track 22 upstream of transfer unit 90 and adjacent restrainer unit 92. Code reader 96 is preferably a bar code reader which will read the bar code on the side of a specimen carrier 12 when held by restrainer unit 92, adjacent reader 96. This information is transmitted to a central control unit so as to identify and locate the particular specimen carrier along the conveyor system 10. Location of code reader 96 adjacent and upstream of each exit gate 36 is desirable so as to permit removal of the specimen carrier from the conveyor system at a particular work station, as required by the programmed information in the control unit.

Referring now to FIG. 9, the lower end of elevator 38 is located adjacent one end of the work station track 40. Platform 126 is oriented such that the top surface of platform 126 is located at the same height or slightly above the top surface 50a of rollers 50 on work station track 40. Thus, specimen carrier 12 may be pushed directly off of platform 126 onto rollers 50.

Pusher apparatus 42 includes a pneumatic cylinder 146 supported on a pair of legs 148 which extend upwardly from a base support 150. Cylinder 146 includes a plunger 152 and is located in alignment with track rollers 50 so as to push specimen carrier 12 across platform 126 and onto rollers 50. A pair of air lines 154 provide the air pressure required to extend and retract plunger 152.

Figure 10:
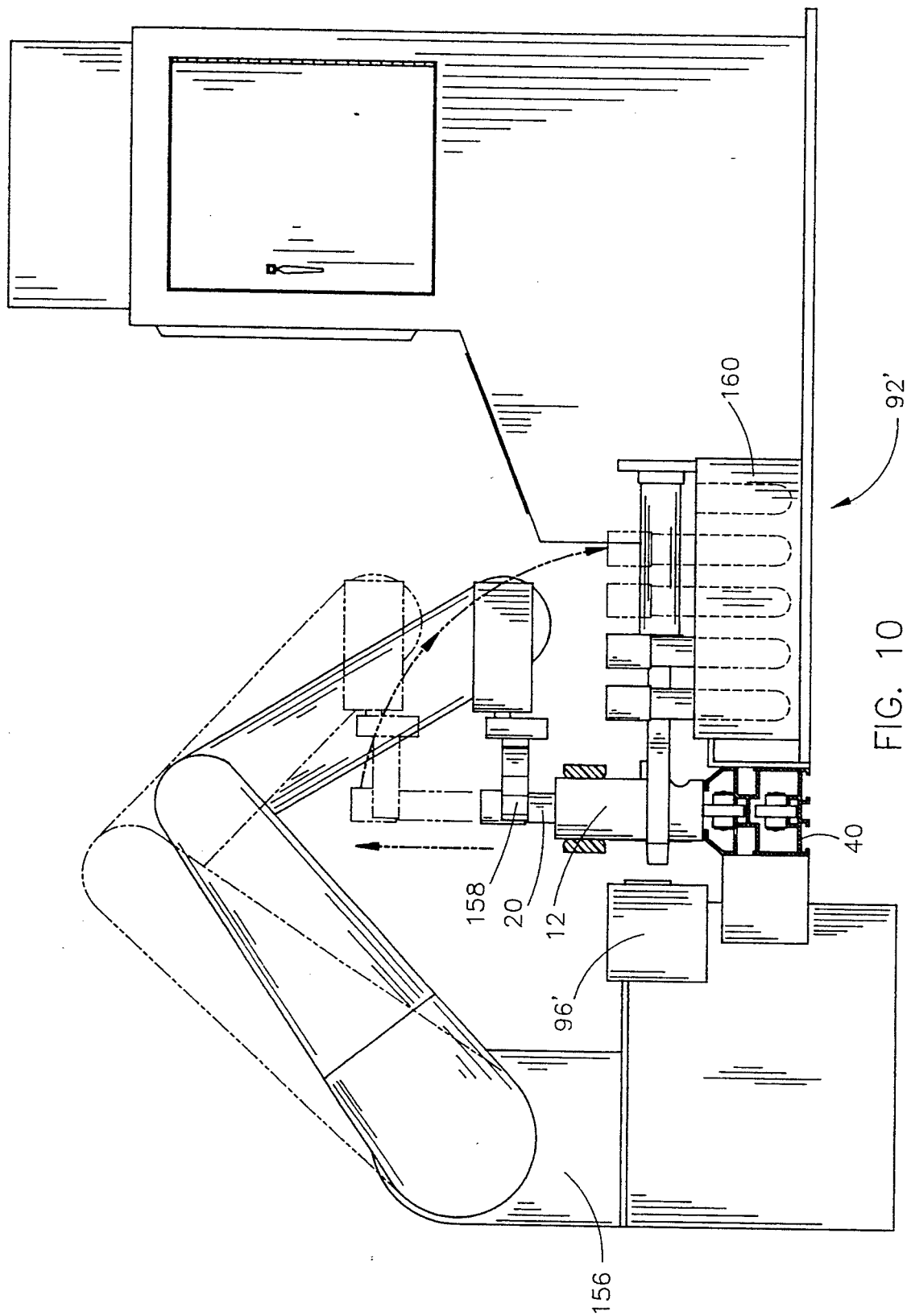
FIG. 10 is a sectional view through a work station track showing the transfer of a specimen tube from a specimen carrier at a work station.

After leaving elevator 38, specimen carrier 12 moves along work station track 40 to the desired work station. FIG. 10 shows one type of work station utilized with the present invention.

Figure 11:
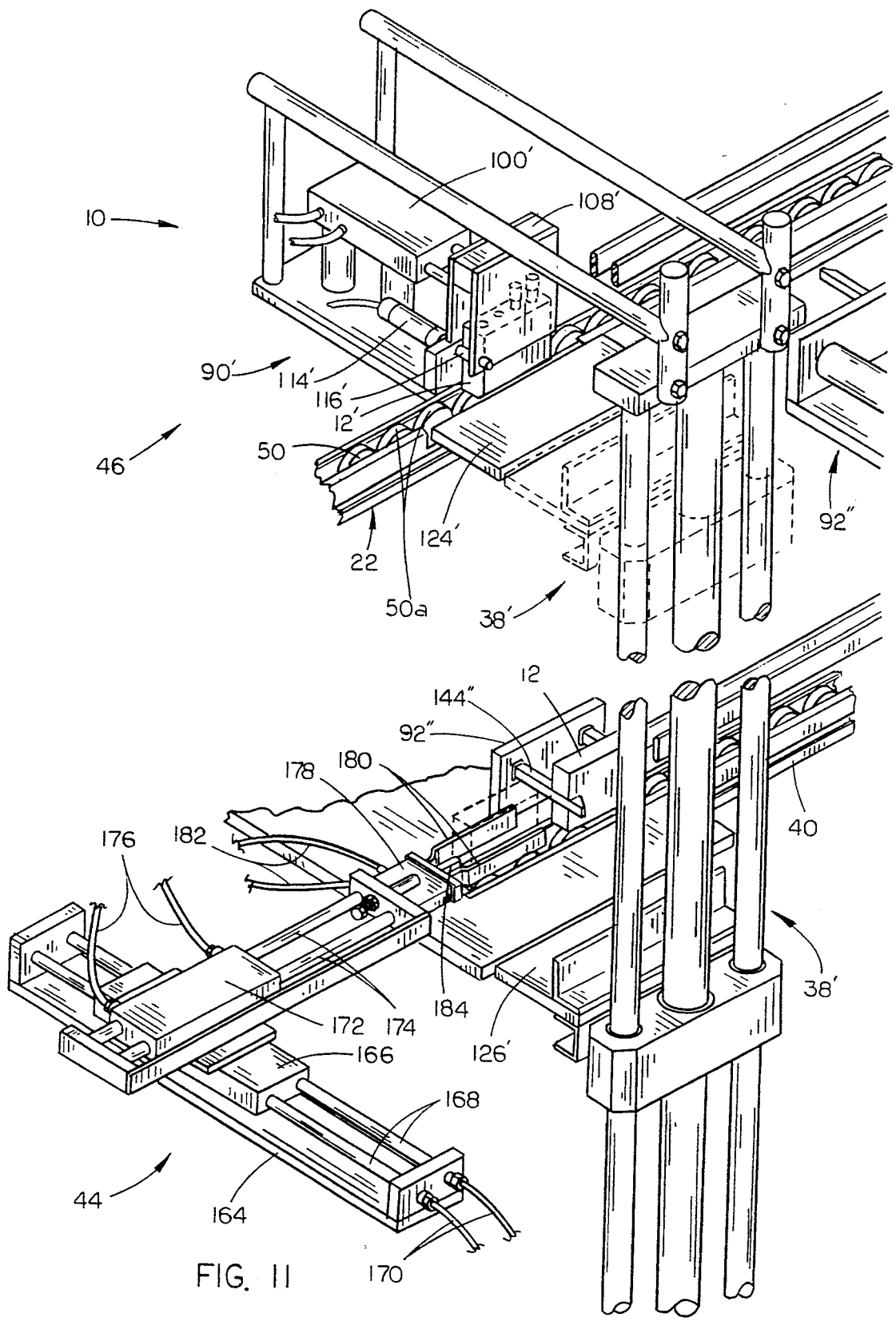
FIG. 11 is a perspective view of an elevator utilized to transfer a specimen carrier from a work station track to the conveyor track.

A restrainer unit 92' is provided to restrain specimen carrier 12 in a predetermined position on conveyor track 40. A robotic arm 156 is provided with an operable jaw 158 so as to remove specimen tubes 20 from specimen carrier 12 and relocate them within a carrier rack 160 of a type permitting one or more specimens to be processed within an analyzer 162. A code reader 96' is located adjacent restrainer unit 92 so as to identify the specimen carrier and specimen tube from which the robotic arm 156 is removing a sample. Robotic arm 156 may also grasp specimen carrier 12 and locate the specimen carrier in a separate storage rack (not shown) until processing of the appropriate specimen tube 20 has been accomplished. The specimen carrier 12 may then be returned to conveyor track 40, and the appropriate specimen tube 20 replaced in carrier 12. The results from analyzer 162 may then be transmitted to the central control unit to permit assignment of specimen carrier 12 to the next appropriate location along conveyor system 10. Referring now to FIG. 11, the downstream end of work station track 40 has a receiver apparatus 44 located to receive a specimen carrier 12 and transfer it to an elevator 38'. Elevator 38' then lifts the specimen carrier up to the entrance gate 46 for entry onto the conveyor track 22 of conveyor system 10.

A restrainer unit 92" is located at the downstream end of work station track 40 to selectively restrain specimen carriers as they approach receiver apparatus 44 along track 40. Receiver apparatus 44 includes a base unit 164 having a carriage 166 operably mounted thereon for movement along a pair of cylinder rods 168. Carriage 166 is preferably operated along cylinder rods 168 by virtue of air lines 170 connected thereto. Base 164 is mounted adjacent the downstream end of conveyor track 40 and perpendicular thereto, such that carriage 166 is operable along a transverse axis perpendicular to work station track 40. A housing 172 is mounted on carriage 166, and has a pair of pneumatically operated shafts 174 projecting therethrough oriented perpendicularly to cylinder rods 168. Air lines 176 are connected to housing 172 to extend or retract shafts 174 from housing 172.

A gripping jaw 178 is mounted on the forward end of shafts 174 and includes a pair of operable arms 180 thereon for gripping a specimen carrier 12. Jaw 178 is moved towards and away from a specimen carrier 12 by the extension or retraction of shafts 174 in housing 172. A pair of air lines 182 connected to jaw 178 operate arms 180 towards and away from each other to selectively grip a specimen carrier 12, as shown in broken lines in FIG. 11.

In operation, arm 144" on restrainer unit 92" will retract to release specimen carrier 12, which will move downstream on track 40 towards receiver apparatus 44. Jaw arms 180 are spaced apart and aligned with track 40 to receive specimen carrier 12 therebetween upon release from restrainer unit 92". A projecting bearing 184 stops movement of specimen carrier 12 at the appropriate position between arms 180, and jaw arms 180 are then activated to grip specimen carrier 12. Carriage 166 is then activated to transfer specimen carrier 12 to elevator platform 126', located immediately adjacent track 40. Once specimen carrier 12 is positioned on elevator platform 126', arms 180 are activated to release the specimen carrier. Housing 172 is then activated to retract shafts 174, thereby retracting jaw 178 and arms 180 to a position clear of vertical movement of elevator platform 126'. Elevator 38' then moves specimen carrier 12 vertically upwardly for entry onto conveyor track 22, as described in more detail hereinbelow.

Entrance gate 46 includes a transfer unit 90' in conjunction with elevator 38' to enter a specimen carrier 12' onto conveyor track 22 of conveyor system 10. A restrainer unit 92''' is mounted upstream of transfer unit 90' and elevator 38' along conveyor track 22, to selectively restrain specimen carriers during the operation of transfer unit 90'. The function of entrance gate 46 is virtually identical to that of exit gate 36, except that the specimen carrier 12' is shifted from the elevator 38' to track 22, rather than the reverse. For this reason, auxiliary platform 124' is mounted on conveyor track 22 with its top surface slightly higher than the top surface 50a of rollers 50 and slightly lower than the upper limit of elevator platform 126'. All other features of transfer unit 90' are the same as those used with transfer unit 90 in exit gate 36, including: cylinder 100' housing 108', auxiliary cylinder 114' and auxiliary arm 116'.

Once specimen carrier 12' has been transferred onto conveyor track 22, as shown in FIG. 11, auxiliary cylinder 114' is operated to retract auxiliary arm 116' to permit specimen carrier 12' to proceed along conveyor track 22. Since housing 108' is aligned over conveyor track 22, additional specimen carriers will pass freely therethrough, until restrained by restrainer unit 92''' to permit operation of transfer unit 90' once again.

Figure 12:
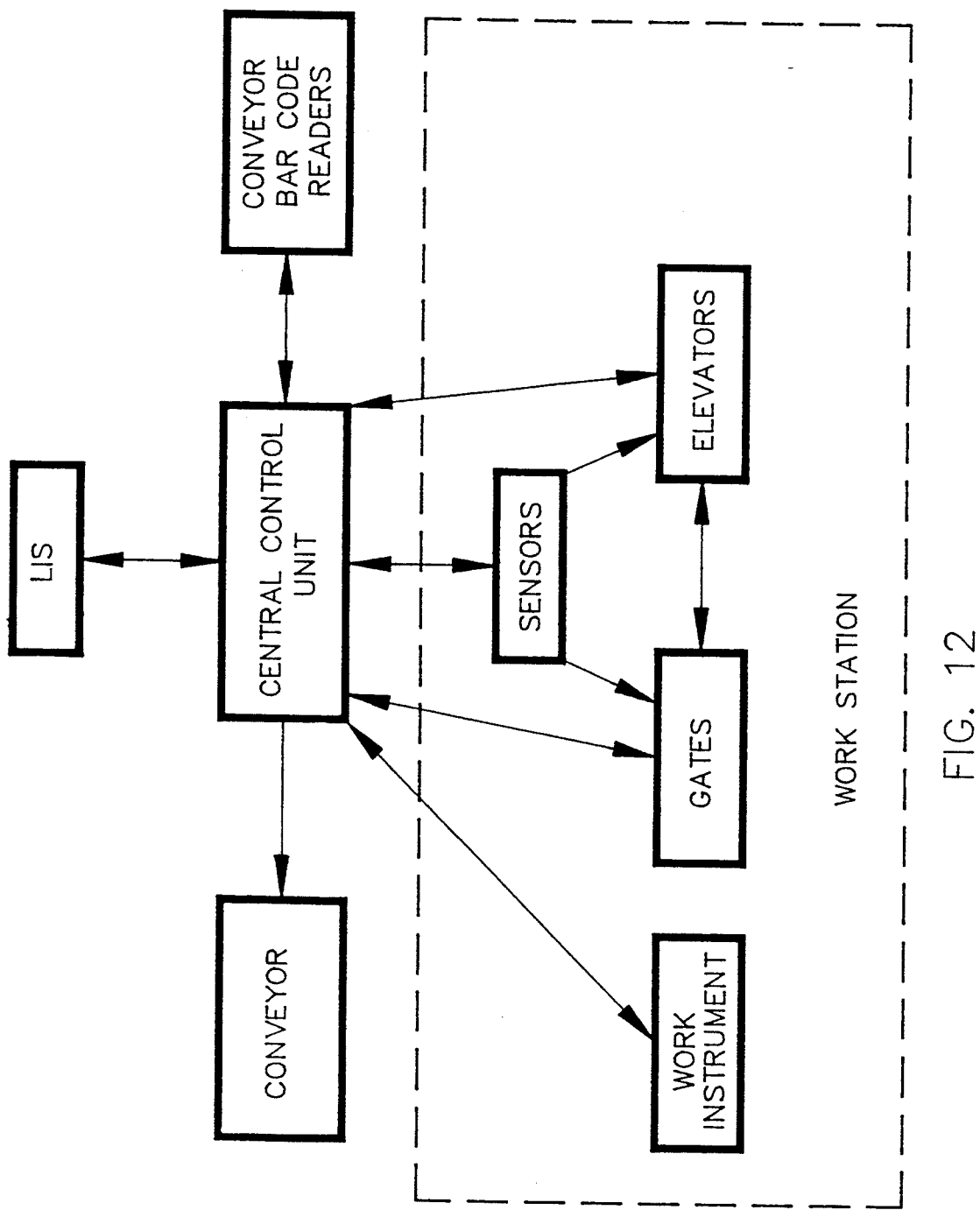
FIG. 12 is a general schematic diagram of the control relationships between the various components of the laboratory automation system.

With reference to FIG. 12, it can be seen that a central control unit interconnects all of the various components of the conveyor system and work stations and also communicates with the LIS. Preferably, the central control unit includes a computer for analysis and processing all of the information necessary to run the automated laboratory of the present invention. The main information received by the control unit comes from bar code readers located along the conveyor system to track the progress of specimens throughout the automated system, as well as from the specified work instruments at each of the work stations which performs tests or other work on the specimens. The information from these two components is analyzed and processed to set the appropriate gates and elevators to move the specimens from one location to another. Sensors at each work station provide information to the gates, elevators and central control unit to more specifically identify the location of a specimen carrier as it moves from the conveyor through the gates and elevators to and from a work station.

Whereas the invention has been shown and described in connection with the preferred embodiment thereof, it will be understood that many modifications, substitutions and additions may be made which are within the intended broad scope of the appended claims. There has therefore been shown and described a laboratory automation system which accomplishes at least all of the above stated objectives.

We claim:

1. An automated laboratory conveyor system, comprising:

a conveyor track for transporting a specimen carrier;
    said conveyor track including:
        a first length of track having upstream and downstream ends; and
        a second length of track having upstream and downstream ends, connected at its upstream end to the downstream end of said first track length;
        said first and second track lengths oriented at an angle with respect to one another to form a corner at the connection thereof;
    said corner connection including:
        a first auxiliary transport surface aligned with said first track length and connected to the downstream end thereof, said first auxiliary transport surface operating at a speed less than that of first track length transport surface, to slow the movement of a specimen carrier thereon;

a second auxiliary transport surface aligned with said second track length and connected to the upstream end thereof;

a downstream end of said first auxiliary transport surface located adjacent to and slightly above an upstream end of the second auxiliary transport surface, to convey a specimen carrier from the first auxiliary transport surface to the second auxiliary transport surface;

said conveyor track further including:

inner and outer spaced-apart guide rails therealong for directing a specimen carrier therebetween, and an operable transport surface for moving a carrier placed thereon;

said track formed in a closed loop and operable to continuously transport said specimen carrier thereon;

means associated with said track for placing a specimen carrier on said track;

means associated with said track for removing a specimen carrier from said track;

a central control unit operably associated with said track for selectively operating said track to transport a specimen carrier;

said central control unit operatively connected to said carrier placing means and said carrier removing means;

said carrier placing means and carrier removing means being operable in response to signals from said central control unit.

2. The system of claim 1, wherein said carrier connection further includes an outward corner piece having an arcuate vertical inward face with a forward end and a rearward end, the forward end generally aligned with said first track length outer guide rail and said rearward end generally aligned with said second track length outer guide rail, to direct a specimen carrier from said first track length to said second track length.

3. An automated laboratory conveyor system, comprising:

a conveyor track for transporting a specimen carrier;

said track formed in a closed loop and operable to continuously transport said specimen carrier thereon;

means associated with said track for placing a specimen carrier on said track;

means associated with said track for removing a specimen carrier from said track;

a central control unit operably associated with said track for selectively operating said track to transport a specimen carrier;

said central control unit operatively connected to said carrier placing means and said carrier removing means;

said carrier placing means and carrier removing means being operable in response to signals from said central control unit;

a receiving station along said track connected to said central control unit and to said carrier placing means;

entry track means for transporting a specimen carrier from said receiving station to said carrier placing means;

said carrier placing means operably responsive to signals from said central control unit to selectively place a specimen carrier on said conveyor track from said entry track;

said receiving station including means for processing information regarding a specimen carrier and a specimen on said carrier, and means for transmitting said processed information to said central control unit;

said central control unit being responsive to said processed information to transmit signals to predetermined ones of said carrier placing means, conveyor track and carrier removing means at predetermined times;

said receiving station being connected with a laboratory information system having identification and instruction data with respect to specimens;

said means for processing information including:

means for marking an individual specimen carrier with identification data corresponding to a specimen carried by the specimen carrier;

means for transmitting instruction data corresponding to a specimen and marked specimen carrier to said central control unit; and said central control unit connected with said laboratory information system and responsive to instruction data transmitted from said receiving station to transmit signals corresponding to a predetermined specimen and specimen carrier;

a first work station for preforming a predetermined test on a specimen carried by said specimen carrier;

a work station conveyor track having a first portion for transporting a specimen carrier from said conveyor track to said work station and a second portion for transporting a specimen carrier from the work station to the conveyor track loop;

first gate means on said conveyor track for moving a specimen carrier from the conveyor track loop to said work station track first portion; and second gate means on said conveyor track loop for moving a specimen carrier from the work station track second portion to said conveyor track loop;

p1 said first and second gate means connected to said central control unit and operable in response to signals from said central control unit;

said first gate means including:

reader means for reading identification data marked on a specimen carrier, connected to said central control unit and operable to transmit said data read from the carrier to said control unit;

retractable arm means for selectively preventing downstream movement of a specimen carrier, connected to said control unit and operable in response to signals therefrom; and means mounted adjacent said track to move a specimen carrier restrained by said retractable arm means, laterally off of said conveyor track;

said means for moving a specimen carrier connected to said control unit and operable in response to signals therefrom;

said means for moving a specimen carrier including:

a cylinder with extendable plunger, mounted generally transversely to said conveyor track;

a housing mounted to said plunger, including a pair of spaced-apart generally vertical side walls, connected by a cross member at their upper ends;

said housing side walls oriented parallel to the direction of travel of a specimen carrier;

said housing moveable with said plunger from a first position with the side walls on opposite sides of the conveyor track permitting passage of a carrier therebetween on said track, and a second position moved transversely to one side of the track;

said housing located adjacent said retractable arm, to move a carrier restrained on said conveyor track by the retractable arm.

4. The system of claim 3, wherein said cylinder is operably connected to said control unit and is operable in response to signals therefrom.

5. The system of claim 3, wherein said work station conveyor track first portion has an upstream end located adjacent said conveyor track at a location directly under said first gate housing when said housing is in the second position, to receive a specimen carrier thereon.

6. The system of claim 3, wherein said work station conveyor track first portion has an upstream end spaced vertically relative to said conveyor track, and further comprising:

elevator means for vertically transporting a specimen carrier between said conveyor track and said work station track; and pusher means for shifting a specimen carrier from the elevator means to the work station track.

7. The system of claim 6, wherein said elevator means includes:

a generally vertical guide shaft extending between the level of the conveyor track and the level of the work station track;

a platform for supporting a specimen carrier, operably mounted on said guide shaft for selective vertical movement thereon; and means connected to said platform for selectively vertically moving the platform.

8. The system of claim 7, wherein said means for moving the elevator platform is operably connected to the control unit, and is operable in response to signals therefrom.

9. The system of claim 8, further comprising a specimen carrier for transport by said conveyor track, including a carrier body having forward and rearward ends, top and bottom walls, and means for conveying a laboratory specimen therein.

10. The system of claim 9, wherein said conveyor track includes inner and outer spaced-apart guide rails for directing said specimen carrier therebetween, and an operable transport surface for moving said specimen carrier thereon;

said housing walls having a length greater than the length of the specimen carrier, and said cross member mounted to said upper side wall ends at a predetermined distance above the top surface of said specimen carriers; and said inner and outer guide rails having an opening formed therein for receiving said moveable housing therethrough.

11. The system of claim 7, wherein said pusher means includes: a cylinder mounted adjacent the upstream end of said work station track, having a plunger extensible from a cylinder housing;

said cylinder plunger moveable between a retracted position, wherein said elevator platform can move vertically thereby, and an extended position, projecting over said platform to a position causing a specimen carrier on the platform to be moved onto the work station track.

12. An automated laboratory conveyor system, comprising:

a conveyor track for transporting a specimen carrier;

said track formed in a closed loop and operable to continuously transport said specimen carrier thereon;

means associated with said track for placing a specimen carrier on said track;

means associated with said track for removing a specimen carrier from said track;

a central control unit operably associated with said track for selectively operating said track to transport a specimen carrier;

said central control unit operatively connected to said carrier placing means and said carrier removing means;

said carrier placing means and carrier removing means being operable in response to signals from said central control unit;

a receiving station along said track connected to said central control unit and to said carrier placing means;

entry track means for transporting a specimen carrier from said receiving station to said carrier placing means;

said carrier placing means operably responsive to signals from said central control unit to selectively place a specimen carrier on said conveyor track from said entry track;

said receiving station including means for processing information regarding a specimen carrier and a specimen on said carrier, and means for transmitting said processed information to said central control unit;

said central control unit being responsive to said processed information to transmit signals to predetermined ones of said carrier placing means, conveyor track and carrier removing means at predetermined times;

said receiving station being connected with a laboratory information system having identification and instruction data with respect to specimens;

said means for processing information including:

means for marking an individual specimen carrier with identification data corresponding to a specimen carried by the specimen carrier;

means for transmitting instruction data corresponding to a specimen and marked specimen carrier to said central control unit; and said central control unit connected with said laboratory information system and responsive to instruction data transmitted from said receiving station to transmit signals corresponding to a predetermined specimen and specimen carrier;

a first work station for performing a predetermined test on a specimen carried by said specimen carrier;

a work station conveyor track having a first portion for transporting a specimen carrier from said conveyor track to said work station and a second portion for transporting a specimen carrier from the work station to the conveyor track loop;

first gate means on said conveyor track for moving a specimen carrier from the conveyor track loop to said work station track first portion; and second gate means on said conveyor track loop for moving a specimen carrier from the work station track second portion to said conveyor track loop;

said first and second gate means connected to said central control unit and operable in response to signals from said central control unit;

restraining apparatus operably mounted upstream of said first gate means for selectively restraining specimen carriers from moving downstream to said first gate means;

restraining apparatus including first cylinder with an extensible arm, mounted adjacent said conveyor track, said arm operable between an extended position projecting over said conveyor track to prevent passage of a specimen carrier, and a retracted positioned permitting passage of a carrier along the conveyor track;

a sensor means for detecting the presence of a specimen carrier restrained by said first cylinder arm;

said first cylinder being operably connected to said control unit and is operably responsive to signals received therefrom;

said sensor means being connected to said control unit and including means for transmitting a signal indicating the presence of a specimen carrier to said control unit;

said restraining apparatus further comprising a second cylinder with an extensible arm, mounted adjacent said conveyor track spaced upstream of said first cylinder, said second cylinder arm operable between an extended position projecting over said conveyor track to prevent passage of a specimen carrier, and a retracted position permitting passage of a carrier along said conveyor track;

a plurality of specimen carriers for selective transport on said conveyor track, each said specimen carrier comprising:

a carrier body having a forward end and rearward end, an inward wall and an outward wall, and top and bottom walls; and means on said body for carrying a laboratory specimen;

said second cylinder arm being spaced upstream from said first cylinder arm a distance at least equal to the length, as measured from the forward to rearward ends, of one of said specimen carriers, to permit retention of a first specimen carrier behind said first cylinder arm while retaining a second specimen carrier behind a second cylinder arm;

said specimen carrier bodies each being further characterized as having a notch formed in the forward end thereof completely though the body from the inward wall to the outward wall, said notch extending rearwardly to a depth sufficient to receive the entire width of one of said restraining apparatus cylinder arms therein, such that the forward end of a specimen carrier abuts the rearward end of a downstream specimen carrier when the carriers are restrained behind the restraining apparatus first arm, and permitting extension of the restraining apparatus second arm into the notch of the upstream carrier to restrain the upstream carrier independently of the downstream carrier.

* * * * *